United States Patent
Li (10) Patent No.: US 10,980,212 B2
(45) Date of Patent: Apr. 20, 2021

(54) CLUMPING DEODORIZER COMPRISING AN ACTIVATED CARBON CORE

(71) Applicant: NESTEC SA, Vevey (CH)

(72) Inventor: James Li, Frontenac, MO (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 109 days.

(21) Appl. No.: 16/193,288

(22) Filed: Nov. 16, 2018

(65) Prior Publication Data

US 2019/0150395 A1    May 23, 2019

Related U.S. Application Data (60) Provisional application No. 62/588,719, filed on Nov. 20, 2017.

(51) Int. Cl.
| | | |
|---|---|---|
| *B01J 20/20* | (2006.01) | |
| *A01K 1/015* | (2006.01) | |
| *A61L 9/014* | (2006.01) | |
| *B01J 20/28* | (2006.01) | |
| *B01J 20/30* | (2006.01) | |
| *B01J 20/32* | (2006.01) | |

(52) U.S. Cl.
CPC .......... *A01K 1/0154* (2013.01); *A01K 1/0152* (2013.01); *A61L 9/014* (2013.01); *B01J 20/20* (2013.01); *B01J 20/2803* (2013.01); *B01J 20/28011* (2013.01); *B01J 20/3042* (2013.01); *B01J 20/3234* (2013.01); *B01J 2220/42* (2013.01)

(58) Field of Classification Search
CPC ........ B01J 20/20; B01J 20/12; B01J 20/3028; B01J 20/3042
See application file for complete search history.

(56) References Cited

U.S. PATENT DOCUMENTS

| | | | | |
|---|---|---|---|---|
| 4,897,309 | A * | 1/1990 | Haas ................. | B01J 20/20 427/214 |
| 6,599,856 | B1 * | 7/2003 | Uchino .............. | B01D 53/02 423/282 |
| 6,890,373 | B2 * | 5/2005 | Nemoto ............. | B01D 53/02 210/504 |
| 7,179,382 | B2 * | 2/2007 | Hiltzik .............. | C01B 32/372 210/633 |
| 9,253,961 | B2 | 2/2016 | Fritter et al. | |
| 9,283,540 | B2 | 3/2016 | Fritter et al. | |
| 9,648,845 | B2 | 5/2017 | Fritter et al. | |
| 10,071,363 | B2 | 9/2018 | Jenkins et al. | |
| 10,377,863 | B2 * | 8/2019 | Kalyanaraman ... | C08G 73/1053 |
| 2005/0005870 | A1 | 1/2005 | Fritter et al. | |
| 2006/0243212 | A1 | 11/2006 | Jenkins et al. | |
| 2007/0017453 | A1 | 1/2007 | Fritter et al. | |
| 2007/0289543 | A1 | 12/2007 | Petska et al. | |
| 2008/0184939 | A1 | 8/2008 | Fritter et al. | |
| 2010/0136336 | A1 | 6/2010 | Borgese et al. | |
| 2010/0269759 | A1 | 10/2010 | Privitera et al. | |
| 2011/0123474 | A1 | 5/2011 | Jenkins et al. | |
| 2017/0339913 | A1 | 11/2017 | Fritter et al. | |
| 2017/0339914 | A1 | 11/2017 | Fritter et al. | |

FOREIGN PATENT DOCUMENTS

| | | |
|---|---|---|
| CA | 2546538 | 11/2007 |
| CA | 2607750 | 5/2008 |
| EP | 0823206 A1 | 2/1998 |
| WO | 9009099 | 8/1990 |
| WO | 9112029 A1 | 8/1991 |
| WO | 9112030 | 8/1991 |

OTHER PUBLICATIONS

International Search Report and Written Opinion to PCT/IB2018/059060 dated Feb. 13, 2019.

* cited by examiner

*Primary Examiner* — Stuart L Hendrickson (57) ABSTRACT

A method of making clumping deodorizer granules can include applying a clumping agent to a particles containing activated carbon to at least partially coat an outer surface of the particles with a distinct layer comprising the clumping agent. Clumping deodorizer granules can include particles containing activated carbon, and an outer surface of each of the particles is at least partially coated with a distinct layer containing a clumping agent. A method of reducing malodor from animal waste can include adding clumping deodorizer granules to a pet litter in a litter box, the clumping deodorizer granules including particles containing activated carbon, and an outer surface of each of the particles is at least partially coated with a distinct layer containing a clumping agent.

18 Claims, 5 Drawing Sheets

CLUMPING DEODORIZER COMPRISING AN ACTIVATED CARBON CORE

CROSS REFERENCE TO RELATED APPLICATIONS

This application claims priority to U.S. Provisional Application Ser. No. 62/588,719 filed Nov. 20, 2017, the disclosure of which is incorporated in its entirety herein by this reference.

FIELD OF THE INVENTION

The present disclosure relates generally to clumping deodorizer granules comprising a core of activated carbon. More specifically, the present disclosure is directed to clumping deodorizer granules comprising particles of activated carbon coated with a layer of clumping agent, such as bentonite.

BACKGROUND

Litter boxes are used by pets such as cats for elimination of urine and fecal matter. A litter box contains a layer of pet litter that receives the urine and fecal matter. The pet litter is granular, absorbent and either non-clumping or clumping. A clumping pet litter is a litter product in which the particles facilitate formation of clumps after the urine and fecal matter is deposited in the pet litter. The clumps are typically sifted from the litter box using a litter scoop and then discarded. Non-clumping pet litter can absorb urine and thus remove urine odors, but replacing soiled non-clumping pet litter without emptying the entire box of litter can be difficult. A deodorizer can be added to the pet litter to absorb malodor from the pet urine and fecal matter.

Activated carbon is an absorbent for odors and can be added to pet litter to control odors by two known methods. First, activated carbon can be added directly into litter as carbon particles. However, the carbon particles cannot directly clump with surrounding litter granules when litter is wetted, and thus the carbon particles reduce the clumping properties of the litter. Another problem with this method is the segregation of activated carbon particles from litter granules. Yet another problem is that granular activated carbon normally has significant amount of black dust. Furthermore, carbon is a black material that reduces product appeal to consumers.

Second, an agglomeration method can enclose activated carbon in pet litter by dry mixing bentonite and activated carbon together. Specifically, bentonite, clay, filler and powdered activated carbon are dry mixed and then agglomerated in pin mixers to produce pet litter comprising the carbon material. One problem with this method is that the quantity of carbon is fixed during manufacturing, and the consumer cannot change it on-site (e.g., at home) according to their needs. Moreover, this method is not very effective to hide the black color of the activated carbon. Additionally, the clumping performance may be reduced when the activated carbon is dry mixed with the bentonite.

SUMMARY

The present inventors surprisingly found that particles of activated carbon coated with a layer of bentonite material not only hide the black color of the activated carbon, but also provide clumping properties when wetted. The deodorizer granules can self-clump to each other or clump with surrounding litter granules when wetted. The density of the deodorizer granules can be comparable to litter material and thus reduce material segregation when the granules are used in a litter box as a deodorizer. The dust level from the deodorizer granules is also minimal due to the method used to prepare the coated granules. The deodorizer granules can be used independently in any application requiring a deodorizer or in any situation to enhance odor-control performance, e.g. deodorizer in a litter box without the unappealing black color or black dust. The consumer can add a different level of deodorizer in pet litter as needed. The deodorizer granules can also be used in any application in which a deodorizer is needed, such as a trash can, a landfill, a farm or a refrigerator.

Accordingly, in a general embodiment, the present disclosure provides a method of making clumping deodorizer granules. The method comprises applying a clumping agent to particles comprising activated carbon to at least partially coat an outer surface of each of the particles with a distinct layer comprising the clumping agent. In another embodiment, the present disclosure provides clumping deodorizer granules made by this method.

In an embodiment, the particles are completely coated by the distinct layer comprising the clumping agent such that all of the outer surface of each of the particles is coated by the distinct layer comprising the clumping agent.

In an embodiment, the method further comprises a binder that adheres the clumping agent to the outer surface of each of the particles, and the method comprises a step selected from the group consisting of (i) dissolving the binder in a liquid to form a solution or suspension that is applied to the particles to form wetted particles to which the clumping agent is then applied, (ii) dry mixing the binder with a powder comprising the clumping agent to form a dry mixture that is applied to the particles, and (iii) a combination thereof. In one embodiment, the binder comprises a hydrocolloid.

In an embodiment, the method further comprises subjecting the clumping deodorizer granules to a rotary coating machine. The method can further comprise drying the clumping deodorizer granules that have been subjected to the rotary coating machine to form dried granules. The method can further comprise separating a portion of the dried granules from the remainder of the dried granules, wherein the portion has sizes with a predetermined size range. The predetermined size range can be −8 to +60 mesh US sieve sizes.

In an embodiment, the method can comprise selecting the particles comprising activated carbon from a plurality of particles comprising activated carbon based on size, before the applying of the clumping agent to the particles. The size can be −10 to +100 mesh US sieve sizes.

In an embodiment, the clumping agent comprises sodium bentonite, and the distinct layer consists essentially of the sodium bentonite.

In an embodiment, the particles consist essentially of the activated carbon.

In an embodiment, the distinct layer is an outermost layer of the deodorizer granules.

In another embodiment, the present disclosure provides clumping deodorizer granules comprising particles comprising activated carbon, and an outer surface of each of the particles is at least partially coated with a distinct layer comprising a clumping agent.

In an embodiment, the particles are completely coated by the distinct layer comprising the clumping agent such that all of the outer surface of each of the particles is coated by the distinct layer comprising the clumping agent.

In an embodiment, the clumping deodorizer granules comprise a binder that adheres the clumping agent to the outer surface of the particles. The binder can comprise a hydrocolloid.

In an embodiment, the deodorizer granules have a size of −8 to +60 mesh US sieve sizes In an embodiment, the particles comprising activated carbon have a size of −10 to +100 mesh US sieve sizes prior to coating with the clumping agent.

In an embodiment, the clumping agent comprises sodium bentonite, and the distinct layer consists essentially of the sodium bentonite.

In an embodiment, the particles consists essentially of the activated carbon.

In an embodiment, the distinct layer is an outermost layer of the granules.

In another embodiment, the present disclosure provides a method of reducing malodor from animal waste. The method comprises adding clumping deodorizer granules to a pet litter in a litter box, the pet litter having a different formulation than the clumping deodorizer granules, the granules comprising particles comprising activated carbon, and an outer surface of each of the particles is at least partially coated with a distinct layer comprising a clumping agent. The pet litter can comprise clay coated with bentonite.

In another embodiment, the present disclosure provides a package comprising a mixture of clumping deodorizer granules and a pet litter, the pet litter having a different formulation than the granules, the clumping deodorizer granules comprising particles comprising activated carbon, and an outer surface of each of the particles is at least partially coated with a distinct layer comprising a clumping agent. The pet litter can comprise clay coated with sodium bentonite.

In another embodiment, the present disclosure provides a method of reducing malodor, the method comprising positioning clumping deodorizer granules in a location comprising a substance creating the malodor, the granules comprising particles comprising activated carbon, and an outer surface of each of the particles is at least partially coated with a distinct layer comprising a clumping agent. The granules can be positioned in a refrigerator or a trash can.

An advantage of one or more embodiments provided by the present disclosure is to provide improved deodorizer granules.

Another advantage of one or more embodiments provided by the present disclosure is to provide methods of making improved deodorizer granules.

A further advantage of one or more embodiments provided by the present disclosure is to overcome the black color and the dust problem of activated carbon particles.

Still another advantage of one or more embodiments provided by the present disclosure is deodorizer granules that also clump with surrounding litter granules when wetted.

Yet another advantage of one or more embodiments provided by the present disclosure is a material containing activated carbon that improves odor control performance of pet litter (e.g., litter comprising clay coated with sodium bentonite) when added to the litter as deodorizer.

Another advantage of one or more embodiments provided by the present disclosure is deodorizer granules that can also be used as regular deodorizer where clumping is not needed, such as a refrigerator or a trash can.

Additional features and advantages are described herein and will be apparent from the following Detailed Description and the Figures.

DETAILED DESCRIPTION

Definitions

Some definitions are provided hereafter. Nevertheless, definitions may be located in the "Embodiments" section below, and the above header "Definitions" does not mean that such disclosures in the "Embodiments" section are not definitions.

As used in this disclosure and the appended claims, the singular forms "a," "an" and "the" include plural referents unless the context clearly dictates otherwise. Thus, for example, reference to "a granule" or "the granule" includes two or more granules.

The words "comprise," "comprises" and "comprising" are to be interpreted inclusively rather than exclusively. Likewise, the terms "include," "including" and "or" should all be construed to be inclusive, unless such a construction is clearly prohibited from the context.

However, the compositions disclosed herein may lack any element that is not specifically disclosed. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. "Consisting essentially of" means that the embodiment comprises more than 50 wt. % of the identified components, preferably at least 75 wt. % of the identified components, more preferably at least 85 wt. % of the identified components, most preferably at least 95 wt. % of the identified components, for example at least 99 wt. % of the identified components.

The term "and/or" used in the context of "X and/or Y" should be interpreted as "X," or "Y," or "both X and Y." Similarly, "at least one of X or Y" should be interpreted as "X," or "Y," or "both X and Y." Where used herein, the terms "example" and "such as," particularly when followed by a listing of terms, are merely exemplary and illustrative and should not be deemed to be exclusive or comprehensive. Any embodiment disclosed herein can be combined with any other embodiment disclosed herein unless explicitly stated otherwise.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, within −5% to +5% of the referenced number, within −1% to +1% of the referenced number, or within −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

The terms "pet" and "animal" are used synonymously herein and mean any animal which can use a litter box, non-limiting examples of which include a cat, a dog, a rat, a ferret, a hamster, a rabbit, an *iguana*, a pig or a bird. The pet can be any suitable animal, and the present disclosure is not limited to a specific pet animal. The term "elimination" means urination and/or defecation by a pet.

As used herein, the term "litter" means any substance that can absorb animal urine and/or decrease odor from animal urine and/or feces. A "clumping litter" or a "clumping deodorizer" forms aggregates when contacted by moisture, the aggregates are distinct from the other litter or deodorizer in the litter box that has not been contacted by moisture. A "clumping agent" binds adjacent particles when wetted. Therefore, "clumping" litter allows consumers to scoop out pet waste using a litter scoop with specific openings, while it is impossible or impractical to scoop out pet waste in "non-clumping" litter. A "non-clumping litter" does not form distinct aggregates. The term "deodorizer" means any substance that absorbs at least a portion of surrounding malodors and can be in a form that is added to pet litter in a litter box.

The term "litter box" means any apparatus that can hold pet litter, for example a container with a bottom wall and one or more side walls, and/or any apparatus configured for litter to be positioned thereon, for example a mat or a grate. As a non-limiting example, a litter box may be a rectangular box having side walls that have a height of at least about six inches.

The term "mesh" is defined by the ASTM E-11 U.S.A. standard specification for sieves. As used herein, "size" of a particle refers to the length of the longest dimension of the particle.

The methods and devices and other advances disclosed herein are not limited to particular methodologies, protocols, and reagents because, as the skilled artisan will appreciate, they may vary. Further, the terminology used herein is for the purpose of describing particular embodiments only and does not limit the scope of that which is disclosed or claimed.

Unless defined otherwise, all technical and scientific terms, terms of art, and acronyms used herein have the meanings commonly understood by one of ordinary skill in the art in the field(s) of the present disclosure or in the field(s) where the term is used. Although any compositions, methods, articles of manufacture, or other means or materials similar or equivalent to those described herein can be used, the preferred devices, methods, articles of manufacture, or other means or materials are described herein.

EMBODIMENTS

An aspect of the present disclosure is a method of making clumping deodorizer granules comprising using a granular activated carbon or agglomerated granular activated carbon. Activated carbon has large surface areas (about 200 to up to 3000 $m^2g^{-1}$, and it is typically available in the form of granules (e.g. −12 to +40 mesh) or powder as extremely fine, dusty granules (e.g., particle size smaller than 150 microns). The present method can comprise providing particles of activated carbon that have a size of −10 to +100 mesh US sieve size (i.e., at least 90% of the particles will pass through a 10 mesh sieve and be retained by a 100 mesh sieve). In another embodiment, the method can comprise providing particles of activated carbon that have a size of −12 to +50 mesh US sieve size (i.e., at least 90% of the particles will pass through a 12 mesh sieve and be retained by a 50 mesh sieve). In some embodiments, the method comprises providing particles of activated carbon that have a size of −12 to 40 mesh. In some embodiments, the method comprises providing particles of activated carbon that have a size of −12 to 30 mesh. For example, commercially available shaker screens may be utilized to separate a portion of the particles of activated carbon with the predetermined size range from the remainder of the particles of activated carbon (e.g., the particles having a size outside of the predetermined range). In some embodiments, the particles of activated carbon are not evenly distributed within the size range.

In one embodiment, the activated carbon has a particle size from about 0.1 mm to about 5 mm, about 0.15 mm to 4 mm, about 0.2 mm to about 3 mm, about 0.25 to about 2.5 mm, about 0.4 mm to about 2 mm, or about 0.42 mm to about 1.7 mm. In another embodiment, the activated carbon has a surface area of about 200 to about 3,000 $m^2g^{-1}$, or about 200 to about 2,000 $m^2g^{-1}$, or about 200 to about 15.00 $m^2g^{-1}$. In another embodiment, the activated carbon has a pore volume of about 0.05 to about 4 $cm^3\ g^{-1}$, about 0.1 to about 3 $cm^3\ g^{-1}$, or about 0.15 to about 2 $cm^3\ g^{-1}$, or about 0.2 to about 1 $cm^3\ g^{-1}$, or about 0.2 to about 0.6 $cm^3\ g^{-1}$.

The activated carbon can be produced from carbonaceous source materials such as bamboo, coconut husk, willow peat, wood, coir, lignite, coal, and petroleum pitch. For example, physical activation can be used to produce the activated carbon, such as by carbonization in which material with carbon content is pyrolyzed at a temperature from 600 to 900° C., in an inert atmosphere with a gas (e.g., argon or nitrogen), or by activation and oxidation in which a raw material or an already carbonized material is exposed to an oxidizing atmosphere of oxygen or steam at a temperature above 250° C., such as 600-1200° C. As another example, chemical activation can be used to produce the activated carbon, such as by impregnating a raw material with an acid, a strong base, or a salt (e.g., phosphoric acid, potassium hydroxide, sodium hydroxide, calcium chloride, or zinc chloride) and then carbonizing the impregnated material at a lower temperature of 450-900° C.

The particles of activated carbon with the predetermined size range can then be coated with a clumping agent such as sodium bentonite. In one embodiment, the method comprises dispersing one or more binders in a liquid such as water to produce a solution with a predetermined viscosity, such as 10 to 2000 centipoise (cP). The viscosity is typically measured using a viscometer, such as a BROOKFIELD DV-II+ at ambient temperature (e.g. about 25° C.). Then the solution can be uniformly added to the particles of activated carbon with stirring to produce wetted particles. Alternatively, the particles of activated carbon can be added to the solution comprising the binder. Then the clumping agent (e.g., sodium bentonite, in powder form) can be added to the wetted particles while slowly and gently stirring, e.g., stirring under 60 rpm to produce coated particles.

Representative clumping agents include, for example, bentonite (such as sodium bentonite), guar gums, starches, xanthan gums, gum Arabic, gum acacia, silica gel, and other minerals, and mixtures a mixture thereof. In one embodiment, the clumping agent comprises bentonite. In another embodiment, the clumping agent comprises sodium bentonite. Sodium bentonite is described in the industry as a "swelling" clay because particles of sodium bentonite enlarge in size and volume when they absorb moisture. In addition, sodium bentonite particles exhibit gel-like qualities when wet that promote clumping of the sodium bentonite particles when liquid (such as urine) is applied. In another embodiment, the clumping agent comprises a mixture of sodium bentonite and one or more different clumping agents, for example, a combination of sodium bentonite and guar gum.

Where sodium bentonite is employed as or in the clumping agent layer, the bulk density of the bentonite is typically in the range of 600 to 1125 $kg/m^3$, or 600 $kg/m^3$, 700 $kg/m^3$, 800 $kg/m^3$, 900 $kg/m^3$, 1000 $kg/m^3$, or 1100 $kg/m^3$. In one particular embodiment, for example, the bulk density of the sodium bentonite is approximately 1125 $kg/m^3$ (approximately 70 $lb/ft^3$).

The bentonite can be applied to the wetted activated carbon particles as a powder, for example a powder having a size of smaller than 100 mesh (0.149 mm). Optionally bentonite powder can be combined with at least a portion of the one or more binders in a dry mixture that is then applied to the wetted activated carbon particle.

The clumping agent (e.g., sodium bentonite powder) can be added in a weight ratio of clumping agent:dry activated carbon particles that is about 1:1 to about 10:1. In some embodiments the weight ratio of clumping agent:dry activated carbon particles is about 1:1 to about 5:1, about 2:1 to about 4:1, or about 3:1. In some embodiments the weight ratio of clumping agent:dry activated carbon particle is about 1:1, about 2:2, about 3:1, or about 4:1. In an embodiment, the clumping agent completely coats the particles of activated carbon such that the entirety of the outer surface of each of the particles of activated carbon is covered with the clumping agent. In one embodiment, the clumping agent coats the particles of activated carbon to form a distinct layer.

The clumping deodorizer granules can be further processed; for example, the mechanical strength of the granules can be improved by subjecting the granules to a rotary coater, such as a high speed rotary coating machine, e.g., operating at 100-2000 rpm, such as about 500 rpm.

The granules can be subjected to drying to remove moisture without substantial damage to the material. For example, the granules can be transferred to a dryer such as a fluidized bed dryer. In some embodiments the granules are placed in an open container and air dried. In other embodiments the granules are dried in an oven. The resultant moisture level can be about 0.25% to about 10%, for example about 6%.

In some embodiments, the method of making clumping deodorizer granules comprises a binder. A non-limiting example of a suitable binder includes a hydrocolloid such as starch (e.g., pre-gelled cereal starch). Another non-limiting example includes cereal starch from one or more of rice, millet, wheat, corn or oats. Other non-limiting examples of suitable binders include other hydrocolloids such as xanthan, guar gum, locust bean gum, gum karaya, gum tragacanth, gum Arabic, alginate, pectin, carrageenan, gelatin, gellan, agar, and cellulose and its derivatives, such as carboxymethylcellulose and methyl hydroxyethyl cellulose.

Other non-limiting examples include polymeric binders such as polyvinyl alcohol, polyacrylamides, polyacrylates, polyethylene glycol, polyvinyl acrylates, polyurethane, and latex. Even inorganic binders such as sodium silicate, bentonite, clay, lime, or cement can also be used for the present disclosure. In one embodiment, the binder is carboxymethylcellulose. In another embodiment, the binder is sodium carboxymethylcellulose.

In some embodiments the solution containing the binder has a viscosity of about 10 to about 2000 centipoise (cP). In some embodiments, the solution containing the binder has a viscosity of about 50 to about 1000 cP. In another embodiment, the solution containing the binder has a viscosity of about 60 to about 700 cP. The viscosity is typically measured at ambient temperature (e.g. room temperature or about 25° C.) using a commercially available viscometer, for example, the BROOKFIELD DV-II+.

In some embodiments, the amount of binder relative to the activated carbon particles is about 0.1% by weight to about 10% by weight. In some embodiments the amount of binder relative to activated carbon particles is about 0.1% by weight to about 1% by weight. In other embodiments, the amount of binder relative to the activated carbon particles is about 0.2% by weight to about 0.5% by weight.

In an embodiment, a portion of the dried granules having a desired size are separated from the other dried granules. One or more sieves can be used to obtain the dried granules having a desired size by separating the dried granules having the desired size from the remainder of the dried granules. In one embodiment the dried granule size is from −12 to +50 mesh US sieve size, i.e., at least 90% of the dried granules will pass through a 12 mesh sieve and be retained by a 50 mesh sieve. In some embodiments, the dried granules are not evenly distributed within the size range. Commercially available shaker screens may be utilized.

Another aspect of the present disclosure is clumping deodorizer granules made by any of the methods disclosed herein. In an embodiment, the amount of the activated carbon relative to the dried granules is about 20 wt. % to about 85 wt. %, for example about 40 wt. % to about 80 wt. %, about 50 wt. %. In one embodiment, the activated carbon core consists essentially of or consists of activated carbon. In another embodiment, the particles of activated carbon that are the core of the dried granules are substantially free from bentonite, i.e., less than 5.0 wt. % bentonite, less than 1.0 wt. % bentonite, or less than 0.1 wt. % bentonite (relative to the total weight of the activated carbon core). In another embodiment, the activated carbon core is completely free of bentonite.

The clumping agent can be about 15 to about 80 wt. %, about 25 to about 70 wt. %, or about 50 wt. % of the dried granule. In an embodiment, the clumping agent forms a layer on the particles of activated carbon, and the layer can include one or more additional components, such as one or more fillers. Nevertheless, in one embodiment the clumping agent layer consists essentially of sodium bentonite. Generally, bentonite is a naturally occurring combination of clay minerals and some non-clay mineral constituents. Bentonite is rich in montmorillonite but may also include other clay and some non-clay mineral constituents. For example, bentonite can include trace amounts of minerals other than montmorillonite, for example feldspar, quartz, calcite, and/or gypsum. Where sodium bentonite is employed as or in the clumping agent layer, it should be understood that sodium bentonite refers to bentonite clay with a considerable percentage of sodium, but may also contain other clays or minerals, including calcium bentonite. Sodium bentonite can be sourced directly through mining operations (natural sodium bentonite) or it can be obtained from conversion of calcium bentonite through an ion exchange process.

In one embodiment of the clumping deodorizer granules, the clumping agent layer is distinct from the activated carbon core (e.g., visually distinct such that a boundary between the core and the coating layer can be visually observed with a microscope). In an embodiment, the clumping agent layer is substantially free from activated carbon, i.e., less than 10 wt. % activated carbon, less than 7 wt. % activated carbon, or less than 5 wt. % activated carbon (relative to the total weight of the clumping agent layer).

In an embodiment, the dried granules have a density similar to litter material, for example a density of about 15 $lb/ft^3$ to about 70 $lb/ft^3$, about 20 $lb/ft^3$ to about 60 $lb/ft^3$, about 25 $lb/ft^3$ to about 50 $lb/ft^3$, or about 35 $lb/ft^3$.

In an embodiment, the dried granules consist essentially of or consist of natural components, and the resultant clumping deodorizer granules consists essentially of or consists of the dried granules. The term "natural components" includes chemically synthesized substances that are identical in structure to a naturally-occurring form of the substance.

Various additives may be optionally included in the dried granules, for example in the activated carbon core and/or in the clumping agent coating. Non-limiting examples of suitable additives include a fragrance, an anti-microbial agent, an anti-sticking agent, an agent for controlling pH, a dye, a coloring agent, a de-dusting agent, a disinfectant, an additional odor control agent, and combinations thereof.

Figure 1:
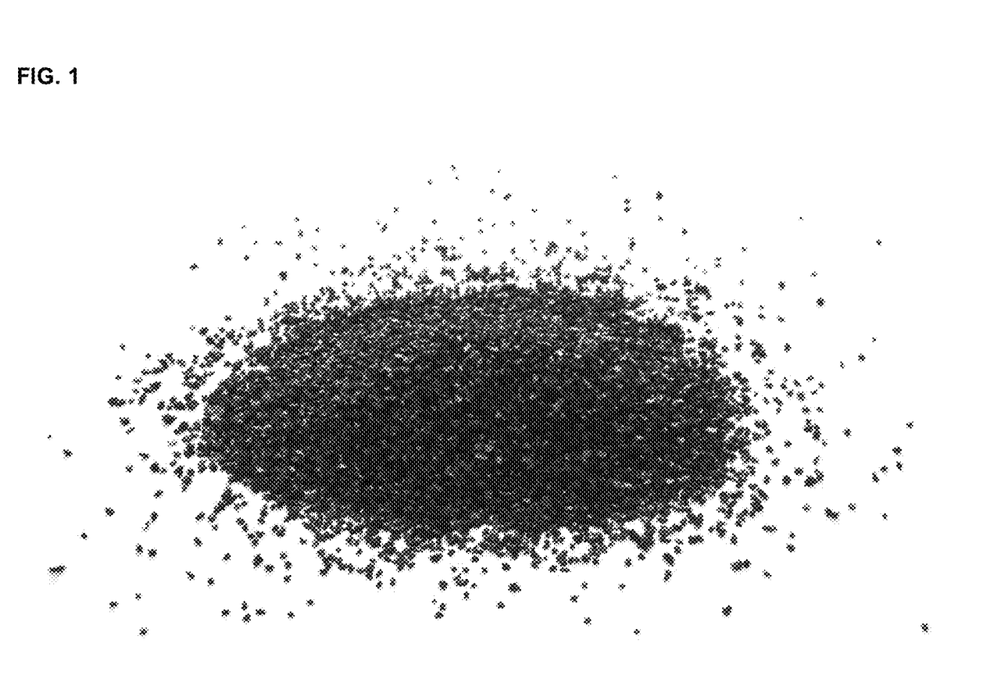
FIG. 1 is an image of granular activated carbon particles before they are coated with a clumping agent according to an embodiment according to the present disclosure.
Figure 2:
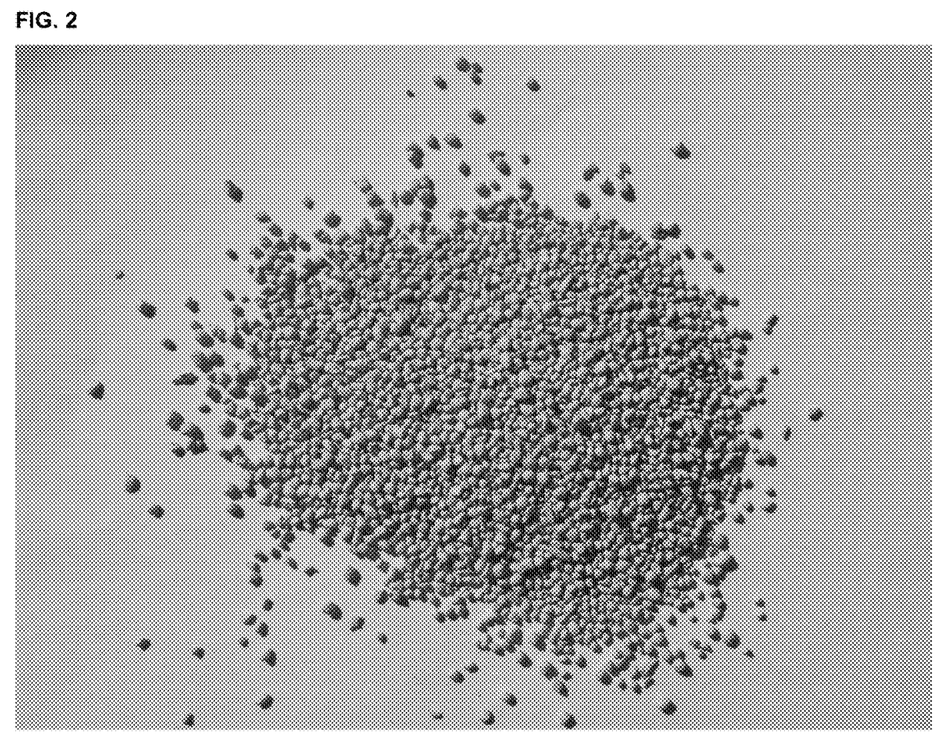
FIG. 2 is an image of granular activated carbon particles coated with a clumping agent, dried and sized according to an embodiment according to the present disclosure.
Figure 3:
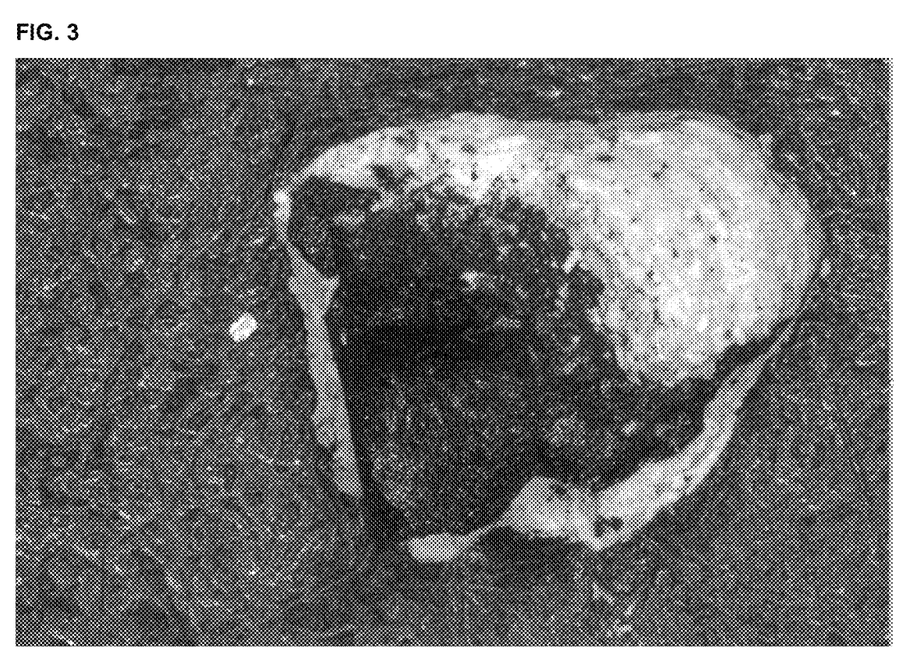
FIG. 3 is an image showing a cross-section view of an embodiment of dried clumping deodorizer granules according to the present disclosure.
Figure 4A:
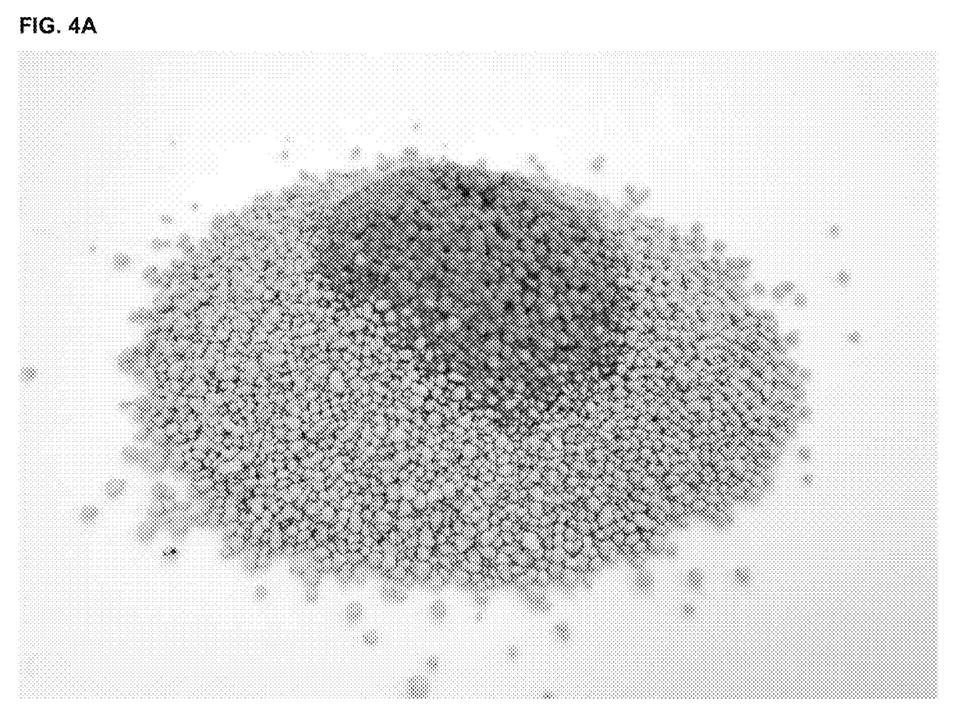
FIG. 4A is an image showing the dried deodorizer granules according to the present disclosure forming a clump when wetted.
Figure 4B:
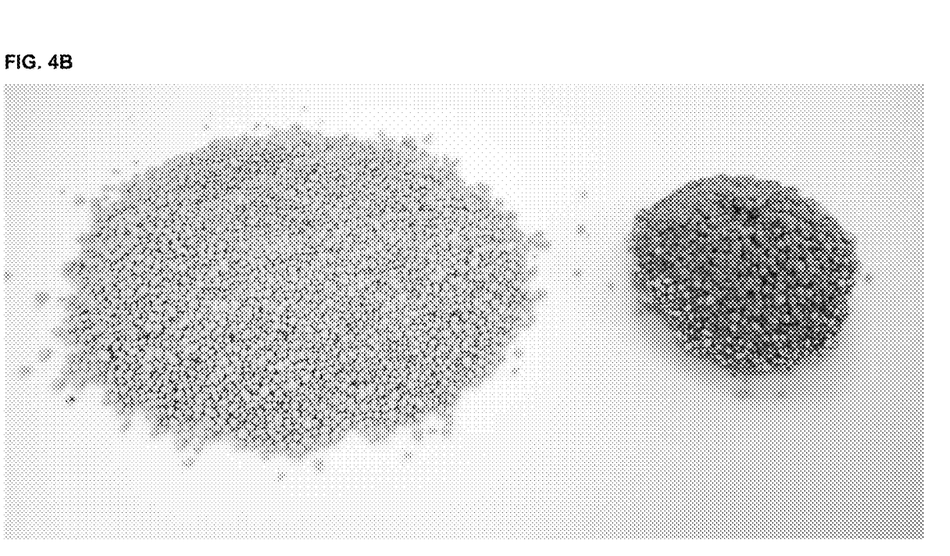
FIG. 4B is an image showing the clump removed from the dried deodorizer granules according to the present disclosure.

Another aspect of the present disclosure is clumping deodorizer granules comprising a core of activated carbon at least partially coated with a distinct layer of a clumping agent (e.g., sodium bentonite). FIG. 1 is an image showing activated carbon particles before coating with a clumping layer; FIG. 2 is an image showing activated carbon particles after coating with a clumping layer and then drying and sizing; and FIG. 3 is an image showing a cross-section view of a dried clumping deodorizer granules. FIG. 4A is an image showing the dried clumping deodorizer granules forming a clump when wetted; and FIG. 4B is an image showing the clump removed from the dried clumping deodorizer granules.

The core of the activated carbon can be substantially free from bentonite. The distinct layer of the clumping agent can be substantially free from activated carbon. The core of activated carbon can consist essentially of the activated carbon. The distinct layer of the clumping agent can consist essentially of the clumping agent (e.g. sodium bentonite).

Another aspect of the present disclosure is a sealed package at least partially enclosing any of the embodiments of the dried granules disclosed herein, for example a sealed box or a sealed bag containing such granules as at least a portion of a clumping deodorizer.

A further aspect of the present disclosure is method of improving odor control of animal waste, the method comprising positioning at least a portion of the clumping deodorizer granules into a litter box containing a pet litter that is a composition having a different formulation than the clumping deodorizer granules (e.g., by pouring the granules from the package into the litter box). Additionally or alternatively, the pet litter can be included in the package with the clumping deodorizer granules so that they are already combined when the user opens the package and/or pours the material from the package into a litter box. In such an embodiment, the granules are homogenously mixed in the litter, for example as about 1 wt. % to about 20 wt. % of the litter, such as about 1 wt. % to about 10 wt. % of the litter or about 1 wt. % to about 5 wt. % of the litter. Nevertheless, the clumping deodorizer granules are not necessarily physically attached to the pet litter, and the granules and the pet litter are distinct constituents that are freely movable relative to each other.

Non-limiting examples of suitable substances for pet litter to which the clumping deodorizer granules can be added include clays, woods, agricultural products (including agricultural by-products), silica gels, and combinations thereof.

Non-limiting examples of suitable clays for the pet litter to which the clumping deodorizer granules can be added include non-swelling clays, swelling clays, and combinations thereof. The clays can be clays that are obtained directly by mining natural clay deposits, synthetic clays, or clays that are derived from the agglomeration of clay particles, e.g., clay particles produced, by litter or other manufacturing processes that involve the use of clays.

Non-swelling clays include kaolinites, illites, ventriculites, attapulgites, sepiolites, and non-swelling smectites. In some embodiments, the non-swelling clays are rich in the following clay minerals: palygorskite-sepiolite, kaolinite, dickite, nacrite, illite, glauconite, celadonite, and phengite. In some embodiments, the non-swelling clays comprise the clay minerals Ca-montmorillonite, kaolinite, and illite.

Swelling clays include smectites and swelling forms of kaolinites, illites, and vermiculites. In some embodiments, the swelling clays contain one or more of hectorite, beidellite, montmorillonite, nontronite, saponite, sauconite, vermiculite, and halloysite. In one embodiment, the clay is bentonite, e.g., a Na-montmorillonite (Na-bentonite). Generally, bentonite is a naturally occurring combination of clay minerals and some non-clay mineral constituents. Na-bentonite is rich in Na-montmorillonite but may also include other clay and some non-clay mineral constituents. In various embodiments, the swelling clays comprise Na-montmorillonite, hectorite, and vermiculite.

When used in combination, the non-swelling and swelling clays can be mixed in any amount suitable for forming the animal litters. Generally, the non-swelling and swelling clays can be mixed in amounts from about 10 to about 90% non-swelling clay and from about 90 to about 10% swelling clay.

Non-limiting examples of suitable woods for the pet litter to which the clumping deodorizer can be added include cedar, pine, oak, maple, *eucalyptus*, aspen, *yucca*, and combinations thereof. In preferred embodiments, the woods comprise cedar, pine, or combinations thereof. In various embodiments, the pine is New Zealand Pine or Southern Yellow Pine, and the cedar is Western Red Cedar. The woods can have any form suitable for functioning as an animal litter, e.g., chips, particles, pellets, crumbled pellets, or crumbles. In preferred embodiments, the woods are cedar, pine, or a combination thereof.

Non-limiting examples of suitable agricultural products for the pet litter to which the clumping deodorizer can be added include alfalfa, corn, corn stalk, corn flour, oat hull, oat stalk, oat flour, barley hull, barley meal, barley stalk, barley flour, wheat hull, wheat straw, wheat flour, soybean hull, soybean meal, soybean floor, rye hull, rye meal, rye straw, rye flour, rice straw, rice hull, sorghum straw, sorghum hull, sunflower seeds, and combinations thereof. In some embodiments, the agricultural products comprise plant material, such as bamboo, lemongrass, switchgrass, catnip, oregano, parsley, rosemary, sage, thyme, valerian root, *alyssum, chrysanthemum*, honeysuckle, hops, lavender, apples, berries, orange peels, orange pulp, sunflower hulls, coffee, tea, or combinations thereof. In other embodiments, the agricultural products comprise sawdust, paper, cellulose, corncob, corn kernel, Distillers Dried Grain (DDG), corn pellet, oaf pellet, barley pellet, wheat middlings, soybean pellet, rye pellet, rice grain, rice pellet, sorghum grain, sorghum pellet, or combinations thereof. In still other embodiments, the agricultural products comprise sunflower seed, almond, pistachio, walnut, pecan, hazelnut, peanut, acorn, wheat middlings, wheat straws, or combinations thereof.

In yet another embodiment, at least a portion of the clumping deodorizer granules can be positioned in a location comprising a substance creating malodor, for example in any application in which an ordinary deodorizer is needed, such as a trash can, a landfill, a farm or a refrigerator.

EXAMPLES

The following non-limiting examples are illustrative of embodiments of the clumping deodorizer granules and methods of making such granules provided by the present disclosure and advantages thereof.

Example 1

(1) 0.25 g of high-viscosity carboxymethylcellulose sodium salt (CMC) from Sigma Aldrich was gradually added into 100 ml of water under vigorous stirring using a blender until totally dissolved. The viscosity of this CMC solution was 76 cP as measured by a BROOKFIELD DV-II+ viscometer at ambient temperature (about 25° C.).

(2) 10 g of coconut-based granular activated carbon particles (−12 to +30 mesh) were gradually added to 5 ml of solution from Step 1, with stirring by hand so that activated carbon particles were uniformly wetted. The amount of binder relative to activated carbon was 0.125% by weight.

(3) 20 grams of sodium bentonite powder was dry mixed with 3 wt. % of CMC powder (high viscosity).

(4) The activated carbon particles from Step 2 were added into a dry mixture of the bentonite and CMC powder from Step 3, with vigorous stirring of the mixture by hand; the bentonite was uniformly coated on the activated carbon particles.

(5) The resultant material was sieved (−12 to +30 mesh) and then put into a box in open air to let it air dry.

The black color of the activated carbon particles was uniformly covered by the bentonite.

Example 2

(1) 0.25 g of high-viscosity carboxymethylcellulose sodium salt (CMC) from Sigma Aldrich was gradually added into 100 ml of water under vigorous stirring using a blender until totally dissolved.

(2) 28 g of coconut-based granular activated carbon particles (−12 to +40 mesh) was gradually added to 26 g CMC solution from Step 1, with stirring gently by hand so that the activated carbon particles were uniformly wetted. The amount of binder relative to activated carbon was 0.23% by weight.

(3) 88 grams of sodium bentonite powder was added into the wet activated carbon particles from Step 2, with stirring of the mixture by hand; the bentonite was uniformly coated on the activated carbon particles.

(4) The mixture from Step 3 was put into a FlackTek laboratory mixing machine at 800 rpm for 15 seconds.

(5) The resultant material was sieved (−12 to +30 mesh) and then dried in an oven at 90° C. for 4 hours.

The surface of the activated carbon particles was uniformly coated with a layer of bentonite. The black color of the activated carbon was essentially covered.

Example 3

(1) 0.50 g of high-viscosity carboxymethylcellulose sodium salt (CMC) from Sigma Aldrich was gradually added into 100 ml water under vigorous stirring using a blender until totally dissolved. The viscosity of the CMC solution was 232 cP as measured by a Brookfield DV-II+ viscometer at ambient temperature (about 25° C.).

(2) 35 g of coconut-based granular activated carbon particles (−12 to +40 mesh) was gradually added to 25 ml of the CMC solution from Step 1, with stirring gently by hand so that the carbon granules were uniformly wetted. The amount of binder relative to activated carbon was 0.36% by weight.

(3) 100 grams of sodium bentonite powder was added into the wet activated carbon particles from Step 2, with stirring of the mixture by hand; the bentonite was uniformly coated on the activated carbon particles.

(4) The mixture from Step 3 was put into a FlackTek laboratory mixing machine at 800 rpm for 15 seconds.

(5) The resultant material was sieved (−12 to +30 mesh) and then dried in an oven at 90° C. for 4 hrs.

The surface of the activated carbon particles was uniformly coated with a layer of bentonite. The black color of the activated carbon was essentially covered.

Example 4

(1) 0.50 g of high-viscosity carboxymethylcellulose sodium salt (CMC) from Sigma Aldrich was gradually added into 100 ml of water under vigorous stirring using a blender until totally dissolved.

(2) 30 g of coconut-based granular activated carbon particles (−12 to +40 mesh) was gradually added to 15 g of the CMC solution from Step 1, with stirring gently by hand so that the activated carbon particles were uniformly wetted. The amount of binder relative to activated carbon was 0.25% by weight.

(3) 30 grams of sodium bentonite powder was added into the wet activated carbon particles from Step 2, with stirring of the mixture by hand; the bentonite was uniformly coated on the activated carbon particles.

(4) The mixture from Step 3 was put into a FlackTek laboratory mixing machine at 800 rpm for 15 seconds.

(5) The resultant material was sieved (−12 to +30 mesh) and then air dried.

The surface of the activated carbon particles was uniformly coated with a layer of the bentonite. The black color of activated carbon was essentially covered, but the outer bentonite layer was loose compared to the sample from Example 3.

Example 5

(1) 0.20 g of high-viscosity carboxymethylcellulose sodium salt (CMC) from Sigma Aldrich was gradually added into 100 ml of water under vigorous stirring using a blender until totally dissolved. The viscosity of the CMC solution was 64 cP as measured by a Brookfield DV-II+ viscometer at ambient temperature (about 25° C.).

(2) 20 g of coconut-based granular activated carbon particles (−12 to +40 mesh) was gradually added to 18 g of the CMC solution from Step 1, with stirring gently by hand so that the activated carbon particles were uniformly wetted. The amount of binder relative to activated carbon was 0.18% by weight.

(3) 75 grams of sodium bentonite powder was added into the wet activated carbon particles from Step 2, with stirring of the mixture by hand; the bentonite was uniformly coated on the activated carbon particles.

(4) The mixture in step 3 was put into a FlackTek laboratory mixing machine at 800 rpm for 15 seconds.

(5) The resultant material was sieved (−12 to +30 mesh) and then dried in an oven at 90° C. for 4 hrs.

The surface of the activated carbon particles was uniformly coated with a layer of bentonite. The black color of the activated carbon was essentially covered. The bentonite layer was well coated on the surface of the activated carbon particles.

Example 6

(1) 0.50 g of high-viscosity carboxymethylcellulose sodium salt (CMC) from Sigma Aldrich was gradually added into 100 ml of water under vigorous stirring using a blender until totally dissolved.

(2) 16 g of coconut-based granular activated carbon particles (−12 to +40 mesh) and 4 g of powdered activated carbon particles were gradually added to 15 g of the CMC solution from Step 1, with stirring gently by hand so that the activated carbon particles were uniformly wetted. The amount of binder relative to activated carbon was 0.375% by weight.

(3) 60 grams of sodium bentonite powder was added into the wet activated carbon mixture from Step 2, with stirring of the mixture by hand to uniformly coat the bentonite on the activated carbon particles.

(4) The mixture from Step 3 was put into a FlackTek laboratory mixing machine at 800 rpm for 15 seconds.

(5) The resultant material was sieved (−12 to +30 mesh US sieve) and then air dried.

The surface of activated carbon particles was uniformly coated with a layer of bentonite and a small amount of carbon powder. The sample shows a dark gray/blue color due to addition of the powdered activated carbon.

Example 7

(1) 0.750 g of high-viscosity carboxymethylcellulose sodium salt (CMC) from Sigma Aldrich was gradually added into 100 ml of water under vigorous stirring using a blender until totally dissolved. The viscosity of the CMC solution was 640 cP as measured by a Brookfield DV-II+ viscometer at ambient temperature (about 25° C.).

(2) 20 g of coconut-based granular activated carbon particles (−12 to +40 mesh) were gradually added to 12 ml CMC solution from Step 1, with stirring gently by hand so that the activated carbon particles were uniformly wetted. The amount of binder relative to activated carbon was 0.45% by weight.

(3) 44 grams of sodium bentonite powder was added into the wet activated carbon mixture from Step 2, with stirring of the mixture by hand so that the bentonite was uniformly coated on the activated carbon particles.

(4) The mixture from Step 3 was put into a FlackTek laboratory mixing machine at 2000 rpm for 15 seconds.

(5) The resultant material was sieved (−12 to +30 mesh) and then air dried.

The surface of the activated carbon particles was uniformly coated with a solid layer of sodium bentonite. The resultant dried granules were essentially dust free, but the sample showed dark gray color instead of gray color.

Example 8

The odor control capability of the clumping deodorizer granules mixed with pet litter was evaluated. A litter sample containing the clumping deodorizer granules and a control litter sample without the clumping deodorizer granules were treated with animal urine and/or fecal matter. After 5 days each litter sample was rated on a scale of 0-100 by a sensory panel trained in the identification of aromatics associated with fecal/urine, ammonia, and fragrance. The results for each sample were averaged. The results are reported in Table 1.

TABLE 1

| Sample | Intensity of Fecal/Urine Smell |
| --- | --- |
| Litter without clumping deodorizer granules (control) | 59.2 |
| Litter with 3 wt. % clumping deodorizer granules | 32.0 |

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A method of making clumping deodorizer granules, the method comprising applying a clumping agent to particles comprising activated carbon to at least partially coat an outer surface of each of the particles with a distinct layer comprising the clumping agent, wherein the clumping agent comprises sodium bentonite, further comprising a binder that adheres the clumping agent to the outer surface of each of the particles, and wherein the method comprises a step selected from the group consisting of (i) dissolving the binder in a liquid to form a solution or a suspension that is applied to the particles to form wetted particles to which the clumping agent is then applied, (ii) dry mixing the binder with a powder comprising the clumping agent to form a dry mixture that is applied to the particles, and (iii) a combination thereof.

2. The method of claim 1, wherein the particles are completely coated by the distinct layer comprising the clumping agent such that all of the outer surface of each of the particles is coated by the distinct layer comprising the clumping agent.

3. The method of claim 1, wherein the distinct layer is an outermost layer of the granules.

4. The method of claim 1, wherein the binder comprises a hydrocolloid.

5. The method of claim 1, further comprising subjecting the clumping deodorizer granules to a rotary coating machine.

6. The method of claim 5, further comprising drying the clumping deodorizer granules that have been subjected to the rotary coating machine to form dried granules.

7. The method of claim 6, further comprising separating a portion of the dried granules from the remainder of the dried granules, wherein the portion has sizes with a predetermined size range.

8. The method of claim 7, wherein the predetermined size range is −8 to +60 mesh US sieve size.

9. The method of claim 1, comprising selecting the particles comprising activated carbon from a plurality of particles comprising activated carbon based on size, before the applying of the clumping agent to the particles.

10. The method of claim 1, wherein the distinct layer consists essentially of the sodium bentonite.

11. The method of claim 1, wherein the particles consist essentially of the activated carbon.

12. Clumping deodorizer granules comprising particles comprising activated carbon, wherein an outer surface of each of the particles is at least partially coated with a distinct layer comprising a clumping agent, wherein the clumping agent comprises sodium bentonite, and further comprising a binder that adheres the clumping agent to the outer surface of the particles, wherein the binder comprises a hydrocolloid.

13. The granules of claim 12, wherein the distinct layer is an outermost layer of the deodorizer.

14. The granules of claim 12, wherein the particles are completely coated by the distinct layer comprising the clumping agent such that all of the outer surfaces of the particles are coated by the distinct layer comprising the clumping agent.

15. The granules of claim 12, wherein the distinct layer consists essentially of the sodium bentonite.

16. The granules of claim 12, wherein the particles consist essentially of the activated carbon.

17. The granules of claim 12, wherein the granules have a size of −8 to +60 mesh US sieve size.

18. The granules of claim 12, wherein the particles comprising activated carbon have a size of −8 to +60 mesh US sieve size prior to coating with the clumping agent.

* * * * *